United States Patent [19]

Stapert et al.

[11] Patent Number: 5,458,600
[45] Date of Patent: Oct. 17, 1995

[54] LOCKING NAIL FOR HOLLOW BONE FRACTURES

[75] Inventors: Jouwert W. J. L. Stapert, Enschede, Netherlands; Klaus F. A. Behrens, Rickling, Germany

[73] Assignee: Howmedica GmbH, Schoenkirchen, Germany

[21] Appl. No.: 985,412

[22] Filed: Dec. 4, 1992

[30] Foreign Application Priority Data

Dec. 7, 1991 [DE] Germany ................... 9115200 U

[51] Int. Cl.⁶ ..................................... A61B 17/72
[52] U.S. Cl. ..................................... 606/63; 606/64
[58] Field of Search ........................ 606/62, 63, 64, 606/67, 68, 72, 73, 99, 104, 105

[56] References Cited

U.S. PATENT DOCUMENTS

| | | | |
|---|---|---|---|
| 4,622,959 | 11/1986 | Marcus | 606/64 |
| 4,875,474 | 10/1989 | Border | 606/63 |
| 4,946,459 | 8/1990 | Bradshaw et al. | |
| 5,041,115 | 8/1991 | Frigg et al. | 606/62 |
| 5,066,296 | 11/1991 | Chapman et al. | 606/64 |
| 5,112,333 | 5/1992 | Fixel | 606/62 |
| 5,122,141 | 6/1992 | Simpson et al. | 606/62 |
| 5,263,955 | 11/1993 | Baumgart et al. | 606/63 |

FOREIGN PATENT DOCUMENTS

| | | |
|---|---|---|
| 551846 | 7/1993 | European Pat. Off. . |
| 2705154 | 2/1977 | Germany . |
| 3541597A1 | 11/1985 | Germany . |
| 8533134 | 11/1985 | Germany . |
| 8907056 | 8/1989 | WIPO . |

*Primary Examiner*—Stephen C. Pellegrino
*Assistant Examiner*—Guy V. Tucker
*Attorney, Agent, or Firm*—Peter C. Richardson; Lawrence C. Akers; Elizabeth O. Slade

[57] ABSTRACT

A locking nail which is used for a plurality of bone cavities is provided in a plurality of lengths. The bone nail is suited for dynamic medical care as well as for subjecting compression and/or distraction forces.

The shaft (10) of the locking nail is hollow and straight and has an outer diameter which is for the most part smaller than the inner diameter of the corticalis. Enlarging the bone cavity is generally not necessary. The nail has at least a cross bore for receiving a bone screw at the first end and a further cross bore for a bone screw at the second end adjacent the driving end. A bore at the second end (18) is formed as an elongate bore (26) and an inner threaded portion is formed at the second end (18), which threaded portion extends into the elongate bore (26) for receiving a screw bolt (54, 62) which may be brought in contact with the shaft of the bone screw (82) extending through the elongate bore (26).

9 Claims, 5 Drawing Sheets

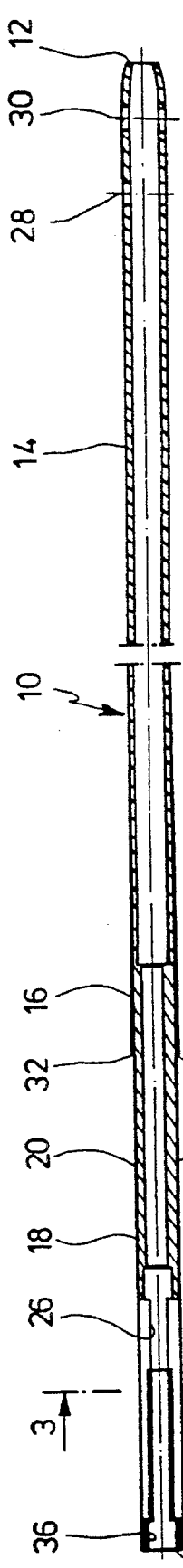
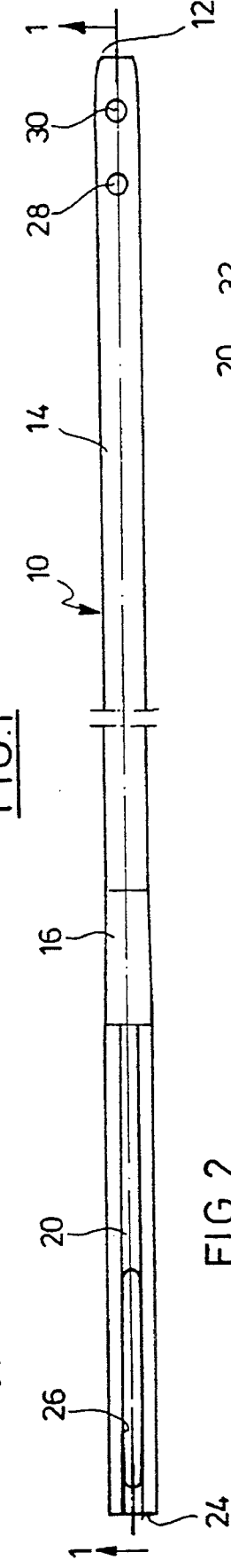
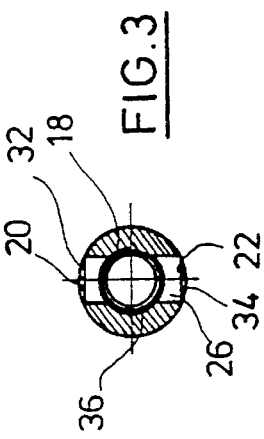
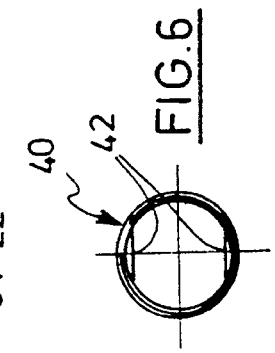
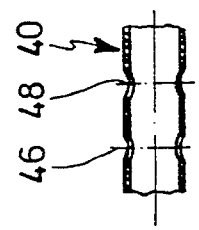
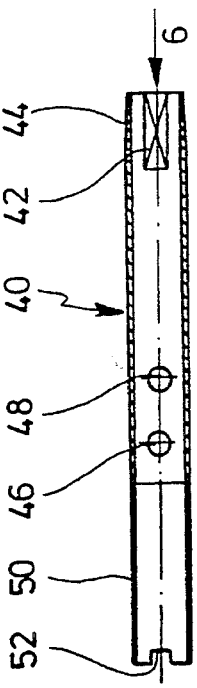

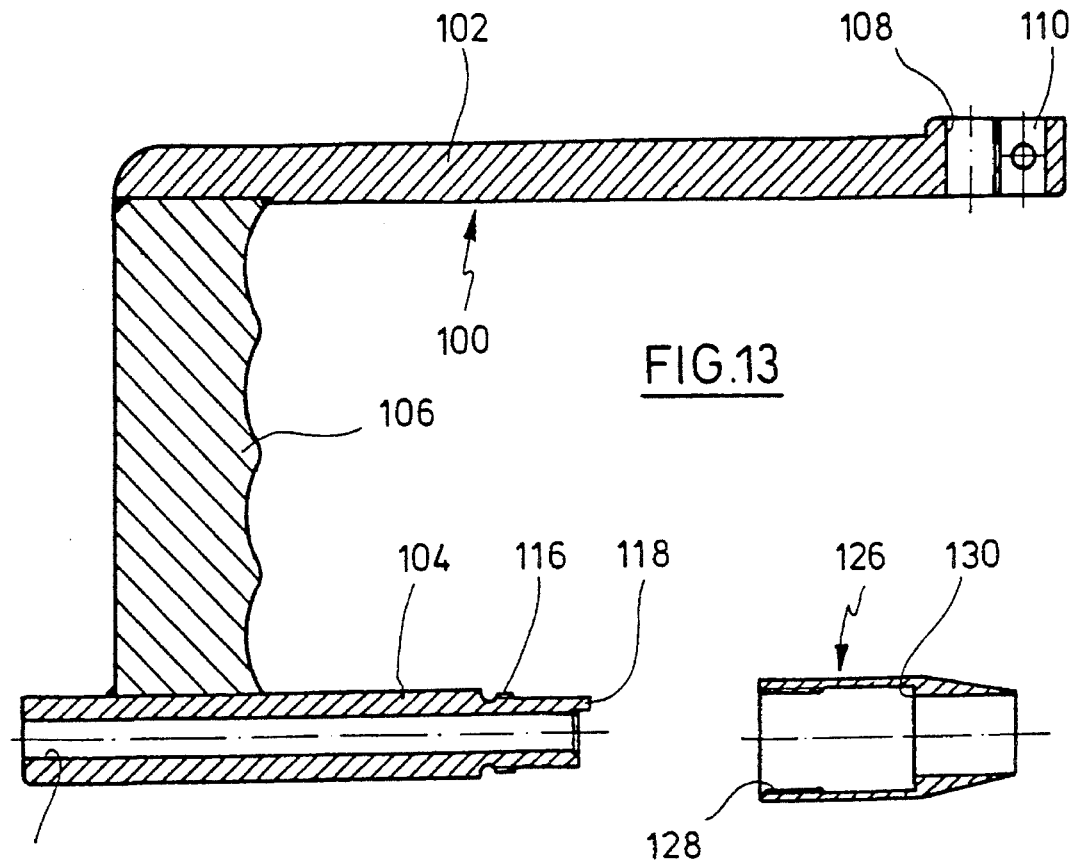
FIG.13
FIG.15
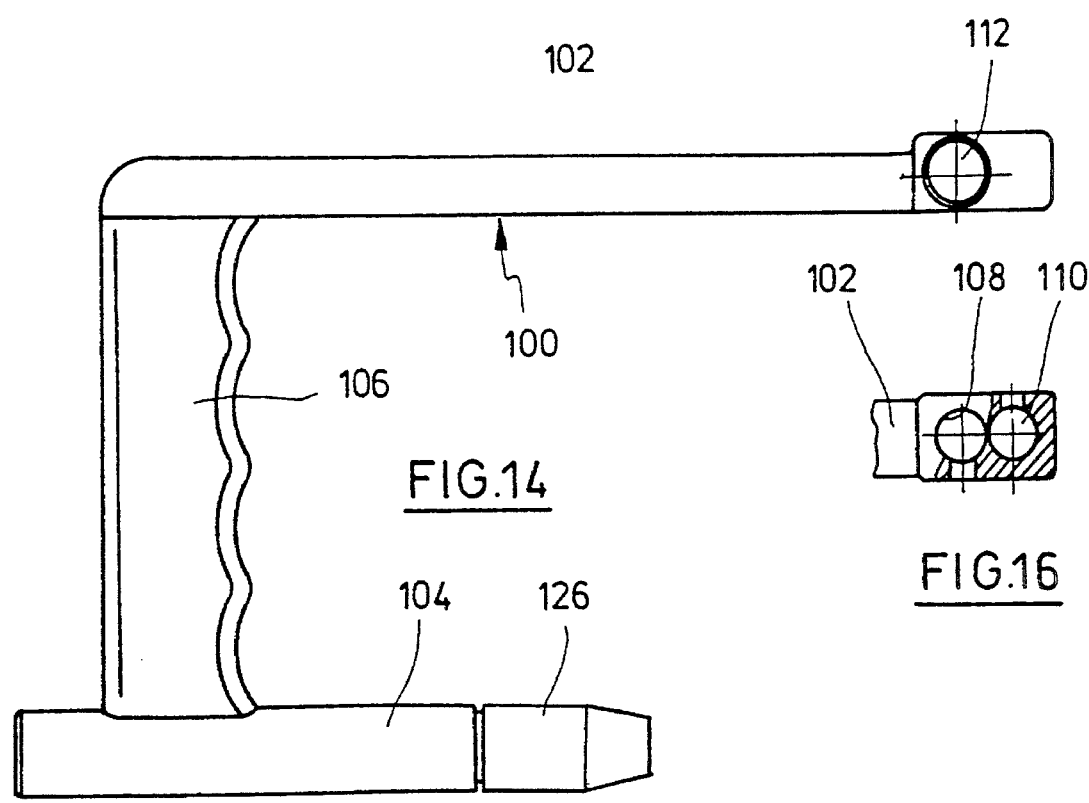
FIG.14
FIG.16

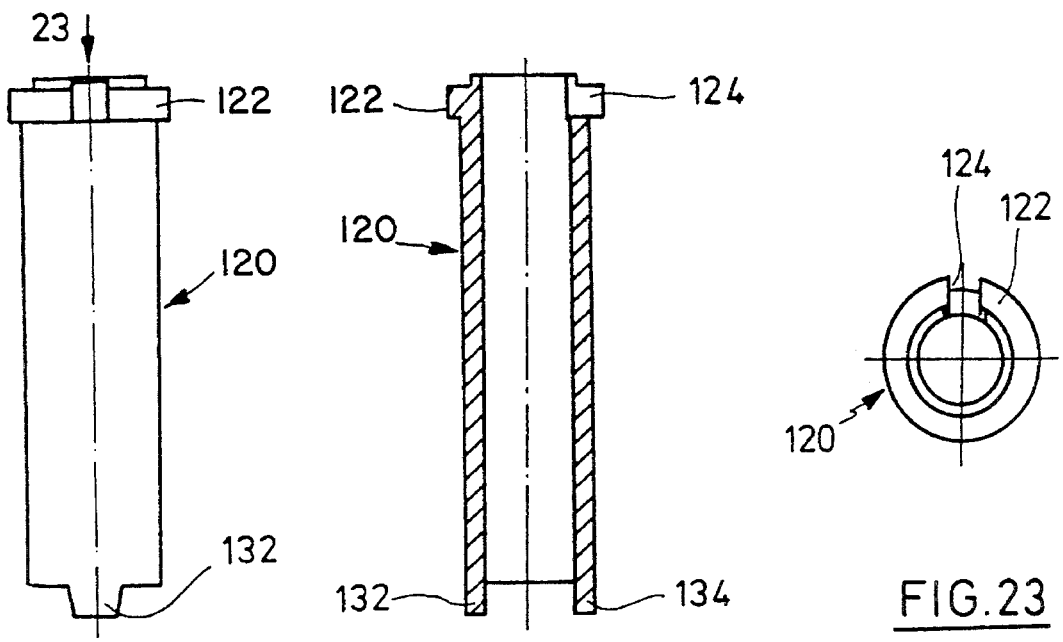
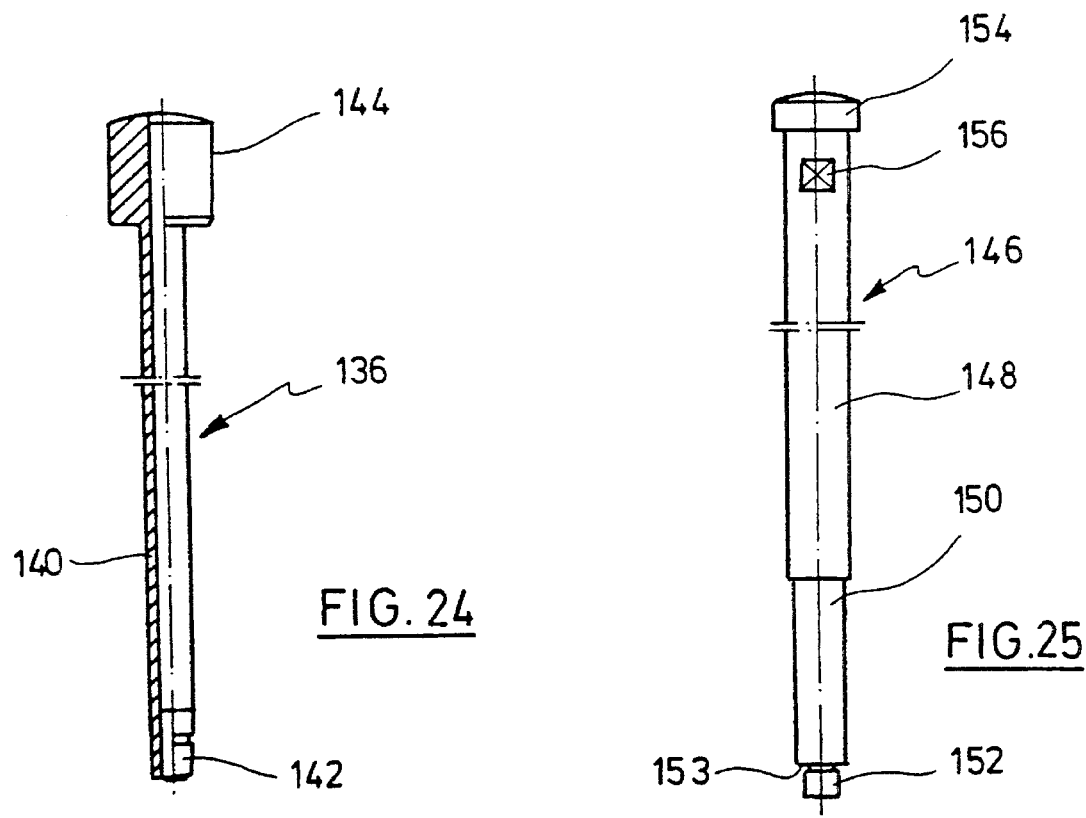

LOCKING NAIL FOR HOLLOW BONE FRACTURES

The present invention refers to a locking nail for the medical care of hollow bone fractures.

BACKGROUND OF THE INVENTION

For the first time German petty patent DE-GM 77 12 901 discloses a locking nail which is used for the osteosynthesis. The locking nail is driven distally or proximally into the hollow bone after preparing the bone cavity. Using conventional nails, the bone cavity is often enlarged by drilling. The ends of the nail are provided with cross bores to receive cortical screws to fix the locking nail in both the axial and rotational direction. This effectively stabilizes the fracture.

The known locking nail is axially slotted which is a drawback when the nail is subjected to a torsion when being driven in, so that bony material is damaged. Therefore, European patent 118 778 disclosed a circular closure of the hollow nail shaft and a trefoiled or starlike profile, for example.

For mounting the cortical screws it is necessary to drill the corticalis in alignment with the cross bores of the nail. There are known numerous positioning means to find the cross bores in the nail and to drill the bores in the corticalis. A number of positioning means use X-rays and a monitor. Other positioning means cooperate with the driving-in end of the nail. The distance of the cross bores from the nail end is known; accordingly this determines the position of the cross bores in the bone. Since, however, the known locking nails are mounted by exerting substantial forces, the nail shaft may twist or bend so that the expected position of the cross bore deviates from the actual position.

Up to now the locking nails have been primarily used for leg bones, wherein a special shape and dimension of the nail shafts have been provided for the femur and the tibia. In particular the shafts have been subjected to a curvature corresponding to the bone shape. It is of course expensive to store a variety of locking nails to be used for different bones.

It is an object of the present invention to provide a locking nail which is used as a standard nail for plurality of bone cavities and which is selected with respect to its length only. Furthermore, the bone nail should be suited for a dynamic medical care as well as for subjecting compression and/or distraction forces.

These objects are solved by the locking nail of the invention.

SUMMARY OF THE INVENTION

The locking nail according to the invention provides a nail shaft which is straight and which has an outer diameter which is for the most part smaller than the inner diameter of the cortecalis. Therefore, enlarging the bone cavity by drilling is not necessary in most cases. This facilitates not only the implantation, but reduces the damage of the bone. For the bone growing process the bone substance should be damaged as little as possible.

The smaller diameter reduces the stability of the nail; but by providing the nail with a straight, unslotted shaft, the nail may transmit substantial forces despite having a smaller diameter. This smaller diameter may be selected such that identical dimensions are selected for the femur and tibia and even for the humerus. Due to the reduced diameter the curvatures of the bone may be disregarded. For increasing stability, a circular cross-section is preferred, at least for the most part of the nail shaft.

The cross bore facing the driving end is formed as an elongated bore and in this portion the nail shaft includes an inner thread to receive a screw. The inner end of the screw may be pressed against a bone screw extending through the elongated bore. The screw thus defines an axial abutment for a static locking. However, when after the implantation or at a later time the fracture shall be dynamized, the screw may be somewhat released so that the bone segments joined through the bone nail have a relative freedom of motion. Conversely by tightening the screw, the fracture may be compressed.

In a further embodiment of the invention a telescopic sleeve may be pushed on the nail shaft from the driving end, which sleeve cooperates with an abutment of the nail shaft and is fixed against rotation on the shaft, wherein the sleeve includes at least a cross bore which is aligned with respect to the elongate bore. Preferably, the cross bore of the telescopic sleeve is aligned with the end of the elongate bore facing away from the driving end when the sleeve contacts the abutment. The range of applications of the inventive nail may be thus extended by using the telescopic sleeve. A static support will be obtained when the cortical screw is located at the end of the elongate bore facing away from the driving end and when the inner end of the screw bolt abuts the cortical screw. However, it is necessary that the telescopic sleeve is axially fixed.

To obtain a compression, the nail shaft is further driven in when the telescopic sleeve is locked. By turning a compressing screw with respect to the inner thread of the nail shaft, the nail shaft and the telescopic sleeve may be displaced towards each other to urge the bone fragments together after the free end of the nail shaft has been locked.

When a distraction shall be obtained, the nail shaft and telescopic sleeve are locked by the cortical screws. By turning a distracting screw with respect to the thread of the telescopic sleeve, the nail shaft and telescopic sleeve are displaced away from each other to move the bone fragments apart.

The nail shaft and the sleeve should be held non-rotationally with respect to each other. Accordingly, the nail shaft may comprise a pair of opposite flats cooperating with a corresponding inner profile of the sleeve. The ends of the flats preferably form abutments for the sleeve. The outer diameter of the sleeve gradually tapers towards the abutment. Thus the change between the nail shaft and the sleeve is formed by a relatively small step which causes no problem for driving and handling the device.

It is of course possible to provide a constant diameter over the whole length of the nail shaft. For forming the flats and for increasing the stability within the region of the elongate bore it is preferred to slightly enlarge the diameter in the region covered by the sleeve. A standard nail may have a diameter of preferably 9 mm. The region covered by the telescopic sleeve is selected to be 10 mm for example.

The cross bore of the nail shaft facing away from the driving end must be detected in a conventional manner when the nail is mounted in the bone. The telescopic sleeve including its cross bore cooperates with a positioning device engaging at least one recess at the free end of the telescopic sleeve, for example.

The locking nail is handled by means of a suitable driving and extracting tool comprising a tool shaft which includes an outer thread portion on the front end and a front abutment and a head including a driving face at the opposite end. The outer thread portion cooperates with an inner thread portion of the nail shaft. The tool shaft may further include an abutment for limiting the driving of the nail when the telescopic sleeve is locked. When the abutment contacts the telescopic sleeve, the nail cannot be further driven in.

According to an embodiment of the invention the positioning device cooperating with the sleeve comprises a U-shaped member comprising a handle, a first leg including a bore for a positioning or drilling sleeve and a second leg to be screwed on the driving end of the nail shaft, wherein the elongate bore of the nail shaft is aligned with the drilling sleeve, when the nail shaft is mounted on the second leg. The second leg preferably comprises an axial bore to receive a nail positioning screw, and the cooperating ends of the second leg and the nail shaft form a non-rotatable assembly when the nail shaft is tightly drawn towards the leg end by the nail positioning screw.

When the nail according to the invention is applied to the humerus by being distally driven in, the telescopic sleeve is not needed. But even then, the position of the bone screw with respect to the elongate bore in the nail shaft may have a different position when used for the femur or the tibia, for example. Thus the telescopic sleeve or, respectively, the nail shaft must have a different relative position with respect to the first leg of the positioning device. According to a further feature of the invention, a separate end piece of a predetermined length is provided for the second leg which may be mounted thereon by a sleeve nut or the like.

The bore in the first leg may receive a tissue protecting sleeve in which a drill guide sleeve is inserted for guiding the drilling tool to drill the corticalis. Preferably a pair of drill guide sleeves of different inner diameter is used. To avoid damaging the drill and to reduce any damage to the bone, a first drill is used to drill the first adjacent corticalis. Thereafter a drill of smaller diameter is used to drill the second corticalis beyond the elongated bore and the bores of the sleeve. The cortical screw is then formed to have a threaded portion close to the head, whereas the remaining shaft is threadless.

As mentioned before, the diameter of the locking nail may have a standard size, disregarding the application. The same applies to the cortical screws. However, the length of the nail shaft and the cortical screw should be suitably selected.

BRIEF DESCRIPTION OF THE DRAWING

Embodiments of the invention are described in more detail in referring to the drawings which show:

FIG. 1 a section of a locking nail according to the invention along line 1—1 in FIG. 2.

FIG. 2 a side view of the locking nail of FIG. 1.

FIG. 3 a section of a nail of FIG. 1 along line 3—3.

FIG. 4 a section through a telescopic sleeve for the nail of FIG. 1.

FIG. 5 a part section of FIG. 4 turned 90° around.

FIG. 6 an end view of the sleeve of FIG. 4 in the direction of arrow 6 in an enlarged scale FIG. 7 a side view of a first embodiment of a compressing screw for the nail of FIG. 1.

FIG. 13 a section of a positioning device.

FIG. 14 a side view of the positioning device.

FIG. 15 a sleeve nut for the positioning device.

FIG. 16 an end view partly in section of the longer leg of the positioning device turned 90° around.

FIG. 21 a side view of an adaptor for the positioning device.

FIG. 22 a side view of the adaptor of FIG. 21.

FIG. 23 an end view of the adaptor of FIG. 21 in the direction of arrow 23.

FIG. 24 a nail positioning screw for the bone nail of FIG. 1 partly in section.

FIG. 25 a side view of a driving tool.

DESCRIPTION OF THE PREFERRED EMBODIMENTS

Figure 7:
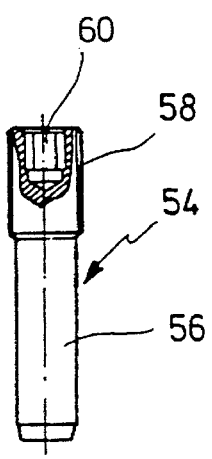
Figure 8:
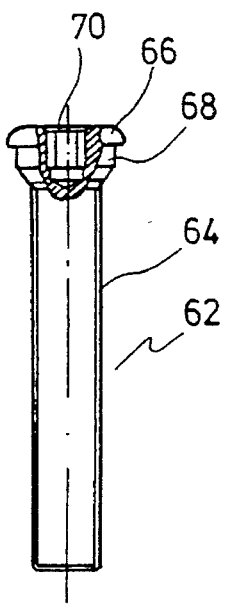
FIG. 8 a second embodiment of a compressing screw.

Before describing the embodiments in detail it should be mentioned that the dimensions shown in the Figures do not correspond to the actual size of the components and are not in proper scale with respect to each other.

A hollow nail shaft 10 comprises a first end 12 which is slightly drawn in. The nail shaft 10 comprises a first portion 14 of circular cross section having an outer diameter of 9 mm, for example. The portion 14 passes over a tapered portion 16 to a second portion 18 including opposite flats 20 and 22. Close to the second end 24, an elongated bore 26 extends through the portion 18. The axis of the elongate bore extends in the same plane as the cross bores 28 and 30 at the first end of the nail shaft 20.

The flats 20, 22 in combination with the tapered portion 16 form small abutments 32, 34. One sees that the portion 18 in front of the bore 26 has a somewhat larger wall thickness than within the region of the bore. In the region of the elongate bore 26 up to the end 24 there is provided an inner thread 36. A telescopic sleeve 40 shown in FIGS. 4 to 6 has a circular cross section and at least partly an inner profile which corresponds to the profile of the nail portion 18, i.e. internal flats as shown at 42. Still further, the outer diameter gradually decreases from one end to form a tapered portion 44. The telescopic sleeve 40 includes a pair of cross bores 46 and 48 as well as an internal thread portion 50 at the other end. At the end of the end portion a pair of opposite recesses 52 is formed.

The sleeve 40 is pushed over the nail portion 18 up to the abutments 32, 34. The sleeve then is non-rotatably mounted on the nail shaft 10. In this position the bore 48 is aligned with the end of the elongate bore 26 facing away from the end 24.

A first compressing screw 54 comprises a shaft portion 56 free of threads and a threaded portion 58 which end includes an inner hexagon 60. The threaded portion 58 can be screwed in the inner thread portion 36 of the nail shaft 10.

The free end of the shaft portion 56 coacts with a bone screw extending through the elongate bore 26. When the screw is located between the ends of the bore 26, it is possible to subject the fractured segments to a compressing force. For example this is necessary when the nail (without telescopic sleeve) is distally driven in the humerus.

A second compressing screw 62 comprises a relatively long threaded portion 64 and a head 66 on which underside a cylindrical portion 68 is formed. The head 66 is provided with an inner hexagon 70 or the like. The threaded portion 64 is screwed in the inner thread portion of the nail shaft 10. The head 66 cooperates with the telescopic sleeve 40 in as much the cylindrical portion 68 enters the sleeve 40 whereas the outwardly projecting head portion contacts the end of the telescopic sleeve. By actuating the compressing screw 62, the sleeve 40 may be shifted along the nail portion 18 under the condition that the sleeve end is remote from the stops 32, 34. For example this is true when after locking the sleeve 40 by inserting bone screws through the bore 46, 48, the nail shaft 10 is further driven in the bone and then fixed. By turning the compressing screw 62, the nail shaft 10 and sleeve 40 are moved towards each other to subject the bone fragments to a compressing force.

Figure 9:
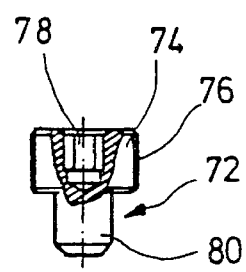
FIG. 9 a side view of a distracting screw for the nail of FIG. 1.

A distracting screw 72 shown in FIG. 9 comprises a head 74 including an external thread portion 76 and an internal hexagon 78 as well as a short shaft portion 80. The head 74 cooperates with the internal thread portion 50 of the sleeve 40, while the shaft portion 80 cooperates with a bone screw extending through the bore 46 to move the sleeve 40 and the nail shaft 10 apart when both are fixed in the bone. This makes it possible to exert a distracting force to the bone fragments.

Figure 11:
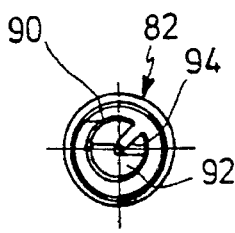
FIG. 11 an end view of the cortical screw in the direction of arrow 11 in FIG. 10.
Figure 10:
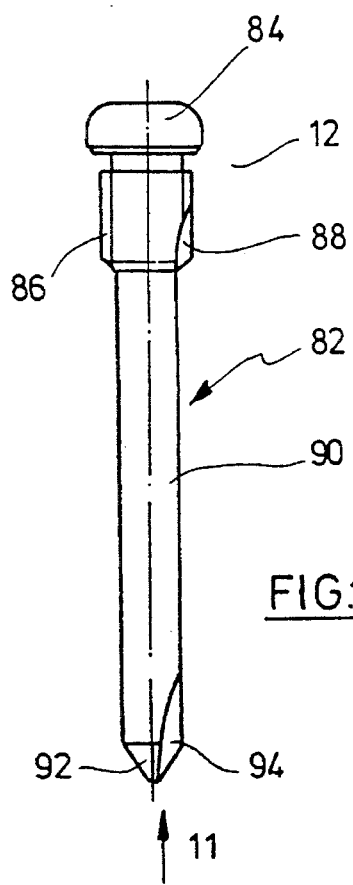
FIG. 10 a side view of a cortical screw for the nail of FIG. 1.
Figure 12:
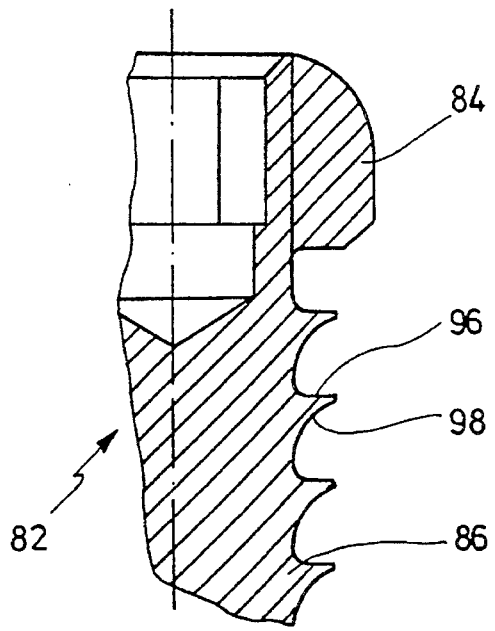
FIG. 12 a section of the part of the screw in FIG. 10 indicated by the circle 12.

FIGS. 10 to 12 illustrate a cortical screw 82 to be inserted through the cross bores 28, 30 and through the elongate bore 26 in the nail shaft and the cross bore 46, 48 of the sleeve 40. The screw comprises a head 84 including an inner hexagon, a threaded portion 86 of relatively short length below the head 84 and a cutting groove 88 provided therein which is formed at the free end. A relatively long threadless shaft portion 90 ending in a conical tip 92 including opposed drilling grooves 94 suspends from the threaded portion 86. FIG. 12 shows that the thread of the portion 86 comprises first flanks 96 extending vertical to the screw axis and second flanks 98 extending under an angle of 60° which facilitates easily turning the thread profile in the drilled bore in the corticalis, whereas the steep flanks 96 serve to create a high back-holding force.

A substantially U-shaped positioning device 100 comprises a first leg 102 and a second leg 104 both being connected through a handle 106. A pair of bores 108, 110 (which are parallel to each other and into which opens a cross bore 112 to receive a fixing screw shown in FIG. 14) are located near the free end of the leg 102.

The second leg 104 comprises an axial bore 114 and a short threaded portion 116 on the right hand portion which has a reduced diameter and an axis parallel nose 118 at the free end thereof. The nose is suited to align an adaptor 120 shown in FIGS. 21 and 22, the end of the adaptor including a radial flange 122 in which a recess 124 is formed. The nose 118 engages the recess 124. A sleeve nut 126 (FIG. 15) comprising an inner thread portion 128 is screwed on the threaded portion 116 of the leg 104. An inner shoulder 130 contacts the radial flange 122 to rigidly mount the adaptor 120 on the leg 104. The other end of the adaptor 120 comprises a pair of noses 132, 134 cooperating with the recesses 52 of the telescopic sleeve 40. The sleeve 40 is thus non-rotatably fixed with respect to the adaptor 120. A nail holding screw 136 comprises a relatively long slim shaft 140 having a free end which comprises a threaded portion 142 of a reduced diameter and the other end comprising a knurled head 144. The nail holding screw 136 is inserted through the leg 104 and the adaptor to be screwed to the inner thread portion 36 of the nail shaft 10 to fixedly connect the nail shaft 10 to the leg 104. In a standard size of the adaptor 120, the axis of the bore 108 in the leg 102 is aligned with the end of the elongate bore 26 facing away from the driving end 24 and with respect to the cross bore 48 of the sleeve 40. The device 100 thus makes it possible to mount the nail and to detect the bores in the nail to properly drill the bore holes in the corticalis. It is still noted that the passage in the leg 104 and the adaptor 120 serve to accommodate a lance for driving in the nail shaft 10 in case a further driving of the nail shaft becomes necessary.

Redriving the nail is performed with a redriving tool 146 shown in FIG. 25. The tool comprises an elongate shaft 148 which is reduced in diameter at 150. The free end carries a portion 152 of a reduced diameter. The opposite end carries a head 154 including a driving face. A pair of opposed flats 156 is shown to apply a rotating tool.

Figure 17:
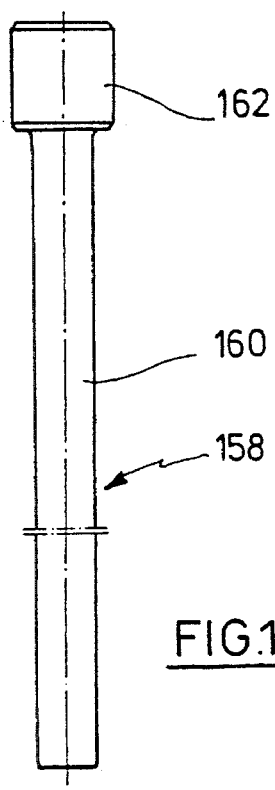
FIG. 17 a side view of a tissue protecting sleeve for the positioning device.
Figure 18:
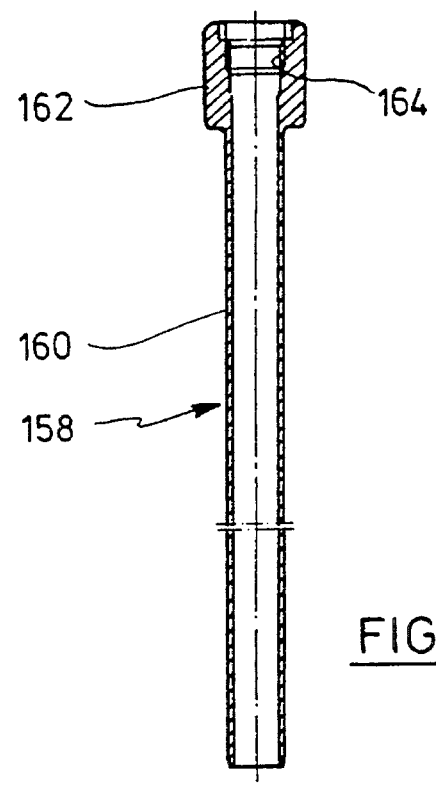
FIG. 18 a longitudinal section of the sleeve of FIG. 17.

The bores 108, 110 of the positioning device 100 may accommodate tissue protecting sleeves of which one sleeve, 158 is shown in FIGS. 17 and 18. The sleeve comprises a hollow shaft 160 and a knurled head 162 including an axial bore with a threaded portion 164. A fixing screw 112 holds the sleeve 158 in position in the bore 108 or 110.

Figure 19:
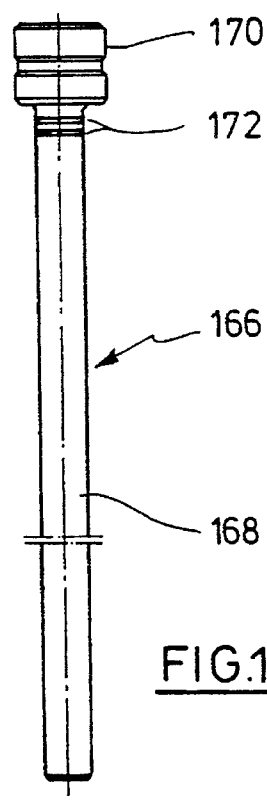
FIG. 19 a side view of a drilling guide sleeve.
Figure 20:
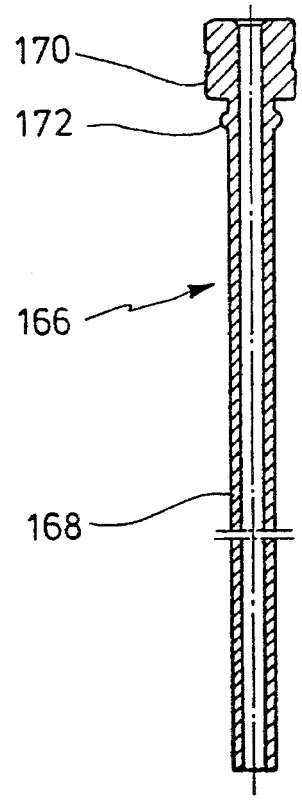
FIG. 20 a longitudinal section of the drilling guide sleeve of FIG. 19.

The protecting sleeve 158 accommodates a drill guiding sleeve 166 shown in FIGS. 19 and 20. The sleeve comprises a hollow elongate shaft 168 and a knurled head 170 as well as a short threaded portion 172 below the head. The threaded portion 172 is screwed in the threaded portion 164 to axially fix the guide sleeve 166 in the protecting sleeve 158. A drilling tool is inserted through the guide sleeve 166 to drill the corticalis, which then receives a bone screw shown in FIGS. 10 to 12. For this, a bore having a larger diameter is first drilled so that two drilling guides leaves are necessary to guide a drilling tool of a smaller diameter.

We claim:

1. A locking nail for the medical care of hollow bone fractures comprising a hollow nail shaft having a first end and a second end, at least one cross bore for receiving a bone screw near said first end and a further cross bore for receiving a bone screw near said second end, wherein the nail shaft (10) is formed straight, having an outer diameter adapted to fit within said hollow bone, said further cross bore near said second end (18) is formed as an elongate bore (26) and an inner threaded portion is formed near said second end (18), which threaded portion extends into the elongate bore (26) for receiving a screw bolt (54, 62) which may be brought in contact with the shaft of a bone screw (82) extending through the elongate bore (26), and including also a telescopic sleeve (40) provided so as to be pushed onto the nail shaft (10) from said second end (24), which sleeve cooperates with stop means (32, 34) of said nail shaft (10) and is non-rotatably connected to said nail shaft and wherein the telescopic sleeve (40) comprises at least one cross bore (46, 48) in alignment with said elongate bore (26), wherein said at least one cross bore (46, 48) of said telescopic sleeve is aligned with an end of said elongate bore (26) facing away from said second end (24) when said telescopic sleeve (40) contacts said stop means (32, 34), and wherein said nail shaft (10) comprises a pair of opposed flats (20, 22) near said telescopic sleeve (40) and wherein said telescopic sleeve (40) has an internal profile which corresponds in shape at least partly to said nail shaft, wherein said flats (20, 22) have ends which form said stop means (32, 34) for telescopic sleeve (40).

2. The locking nail of claim 1, wherein said nail shaft (10) being outside the telescopic sleeve (40) has a slightly smaller diameter than the remaining nail shaft when the telescopic sleeve (40) contacts the stop means (32, 34).

3. The locking nail of claim 2, wherein the diameter of the nail shaft (10) in the region of the nail shaft (10) lying outside said telescopic sleeve is about 9 mm.

4. The locking nail of claim 3, wherein said nail shaft (10) has a wall thickness between said stop means and said elongate bore which is larger than in the remaining region.

5. The locking nail of claim 3, wherein the diameter of said nail near the telescopic sleeve (40) is about 10 min.

6. The locking nail of claim 5, wherein the outer diameter of the telescopic sleeve (40) gradually tapers towards a first end which contacts said stop means (32, 34).

7. The locking nail of claim 6, wherein said telescopic sleeve (40) has a free end which comprises at least one recess (52) for engaging a positioning device (100).

8. The locking nail of claim 7, wherein the telescopic sleeve (40) comprises an internal thread portion (50) near said free end to receive a distracting screw (72).

9. A locking nail for repairing hollow bone fractures comprising (1) a hollow nail shaft
  a. having a first end, a second end, a first cross bore for receiving a bone screw located near said first end, and a second cross bore for receiving a bone screw located near said second end, wherein said nail shaft is substantially straight and has an outer diameter which is smaller than the inner diameter of said hollow bone, wherein an elongated cross bore is located near said second end and an inner threaded portion located near said second end extends into said elongated cross bore for receiving a screw bolt, wherein said nail has stop means;

(2) a telescopic sleeve to be pushed onto said second end of said nail shaft and which cooperates with said stop means of said nail shaft, wherein said telescopic sleeve comprises at least one cross bore in alignment with elongated cross bore of said nail shaft, wherein said at least one cross bore of said telescopic sleeve is aligned with an end of said elongated cross bore facing away from said second end of said nail shaft when said telescopic sleeve contacts said stop means, wherein said nail shaft comprises a pair of opposed flats located near said telescopic sleeve, wherein said telescopic sleeve has an internal profile which corresponds at least in part to said nail shaft, and wherein said opposed flats have ends which form said stop means for said telescopic sleeve.

* * * * *